United States Patent
Raidel et al.

(10) Patent No.: US 6,573,424 B1
(45) Date of Patent: Jun. 3, 2003

(54) ABSORBENT ARTICLE HAVING A COVER LAYER INCLUDING A POLYMERIZED ALKENE

(75) Inventors: Maria Raidel, Nürnberg (DE); Franz Aschenbrenner, Kastl (DE)

(73) Assignee: Hakle-Kimberly Deutschland GmbH, Koblenz (DE)

( * ) Notice: Subject to any disclaimer, the term of this patent is extended or adjusted under 35 U.S.C. 154(b) by 0 days.

(21) Appl. No.: 09/269,493

(22) PCT Filed: Sep. 19, 1997

(86) PCT No.: PCT/EP97/05160
§ 371 (c)(1),
(2), (4) Date: Jan. 10, 2000

(87) PCT Pub. No.: WO98/14151
PCT Pub. Date: Apr. 9, 1998

(30) Foreign Application Priority Data

Sep. 30, 1996 (DE) .......................... 196 40 451

(51) Int. Cl.⁷ ................................. A61F 13/15
(52) U.S. Cl. ................. 604/379; 604/385.101; 604/378
(58) Field of Search ...................... 604/378.38, 385.101

(56) References Cited

U.S. PATENT DOCUMENTS

| | | | | |
|---|---|---|---|---|
| 3,844,288 A | * | 10/1974 | Kiela | 128/287 |
| 4,649,909 A | * | 3/1987 | Thompson | 128/156 |
| 5,607,414 A | * | 3/1997 | Richards et al. | 604/378 |
| 5,624,422 A | * | 4/1997 | Allen | 604/385.1 |
| 5,662,633 A | * | 9/1997 | Doak et al. | 604/378 |
| 5,804,518 A | * | 9/1998 | Sakai et al. | 442/370 |
| 5,827,254 A | * | 10/1998 | Trombetta et al. | 604/378 |
| 5,961,505 A | * | 10/1999 | Coe et al. | 604/378 |
| 6,241,714 B1 | * | 6/2001 | Raidel et al. | 604/378 |

FOREIGN PATENT DOCUMENTS

| | | | |
|---|---|---|---|
| DE | 92 18 991 | 9/1996 | A61F/13/46 |
| EP | 119 919 | 9/1984 | A61F/5/44 |
| EP | 343 941 | 11/1989 | A61F/13/18 |
| EP | 570 016 | 11/1993 | A61F/13/15 |
| GB | 2 254 255 | * 7/1992 | A61F/13/48 |
| WO | 97/33546 | 9/1997 | A61F/13/46 |

\* cited by examiner

Primary Examiner—Dennis Ruhl
Assistant Examiner—Michael Bogart
(74) Attorney, Agent, or Firm—Pauley Petersen Kinne & Erickson

(57) ABSTRACT

The invention concerns an absorbent article, in particular a sanitary towel, having the following structure: a lower layer which faces the body when the absorbent article is in use and is impermeable to fluid; a primary accumulation layer which is disposed above the fluid-impermeable layer; a secondary accumulation layer disposed above the primary accumulation layer; a compensation layer disposed above the secondary accumulation layer; a cover layer which is disposed above the compensation layer and has a central opening; and a fluid-permeable upper layer which faces the body when the absorbent article is in use.

32 Claims, 5 Drawing Sheets

ABSORBENT ARTICLE HAVING A COVER LAYER INCLUDING A POLYMERIZED ALKENE

FIELD OF THE INVENTION

The present invention relates to an absorbent article.

BACKGROUND OF THE INVENTION

Absorbent articles have been known for a long time as sanitary articles. They are used, for example, as diapers, incontinence pads or sanitary napkins. Such absorbent articles are capable of absorbing and retaining liquid body exudates, such as urine, menstrual fluid or blood. Sanitary napkins, for example, are used to absorb fluids discharged before, during and after menstruation. Sanitary napkin s are worn on the outside of the body (externally) and thus differ in so far from tampons which are inserted into the female vagina and can thus be referred to as "internal" products.

The use of known absorbent articles is frequently disadvantageous in so far as the bodyside surface, after liquids have been discharged thereon, comprises wet areas which causes discomfort to the wearer. Tests showed that conventional sanitary napkins rewet if only about 5% of the theoretical liquid absorption capacity of the sanitary napkin has been utilized. Moreover, the discharged body fluids often leave visible residues on the surface of the absorbent article. This causes the user of the article to change the absorbent article more often than it would be necessary as far as the absorbency for liquids is concerned.

SUMMARY OF THE INVENTION

It is an object of the present invention to provide an absorbent article, wherein the absorbency of the liquid storage material of the absorbent article is optimally utilized so that as few traces of use as possible are visible on the bodyside surface of the absorbent article, even after prolonged use.

The absorbent article of the invention has the following structure. A liquid-impermeable layer is provided on the side which is away from the wearer's body when said absorbent article is in use. A primary storage layer is provided above said liquid-impermeable layer. A secondary storage layer is provided above said primary storage layer. A compensation layer is provided above said secondary storage layer, and a cover layer is provided above said compensation layer, said cover layer comprising a central opening. The cover layer comprises a mixture of pulp and polymerized alkene, wherein said mixture comprises at least 50% by weight polymerized alkene. Finally, the absorbent article of the invention includes a liquid-permeable top layer which is disposed toward the wearer's body when the absorbent article is in use.

It was found to be particularly suitable for the secondary storage layer to include at least one densified section. Preferably, the at least one densified section extends in longitudinal direction of said article. The at least one densified section should be disposed within the projection of said central opening of said cover layer on said secondary storage layer. Particularly suitable results have been achieved with a secondary storage layer which includes at least five densified sections.

Pulp, for example, is suitable as a material for the secondary storage layer. Local densifications in the secondary storage are obtainable, for example, by embossing grooves into the storage. The storage material positioned below the embossed grooves is thereby densified, while the grooves contribute to a targeted liquid transfer on the storage layer and the absorbent article, respectively.

The cover layer, which includes the central opening, is made of a mixture of pulp and polymerized alkene. The mixture preferably includes at least 50 wt. % of polymerized alkene. Excellent results have been achieved with a polymerized alkene content of from 50 to 80 wt. %, in particular 60 wt. %. The cover layer may also be constructed of two layers such that a first layer of a mixture of pulp and polymerized alkene is applied on a second carrier layer of polymerized alkene. The first layer of pulp and polymerized alkene communicates with said liquid-permeable layer disposed toward the wearer's body when said absorbent article is in use, and said second carrier layer communicates with said compensation layer. Preferred polymerized alkenes are polyethylene, polypropylene and mixtures of polyethylene and polypropylene. Moreover, the cover layer may contain a pigment such as titanium oxide.

It is favorable for the material of the compensation layer to be made from a nonwoven material. The nonwoven material may contain polymerized alkene and/or bicomponent fibers. Furthermore, the surface of the compensation layer which is disposed toward the storage layer may be coated with a surface-active substance which may contain, for example, silicone. The primary storage layer, for example, may consist of an UCTAD material, tissue fluff or a polymer alkene. It is advantageous for the primary storage layer to be constructed such that the peripheral sections thereof are folded inwardly and overlap each other.

Both the liquid-impermeable layer and the liquid-permeable layer may be made using by a polymerized alkene, such as, for example, polyethylene, polypropylene or a mixture thereof. In order to fasten the absorbent article to a garment, the liquid-impermeable layer preferably includes at least one adhesive element and/or adhesive layer. Moreover, the absorbent article of the invention may include laterally disposed flaps. The absorbent article of the invention is preferably used as sanitary product, in particular as sanitary napkin or feminine care liner.

A preferred UCTAD (uncreped through air-dried) material may also be used as primary storage layer. The material includes at least 10 wt. % of high yield pulp fibers, based on its dry weight. A wet strength agent is added in an amount which causes the ratio of wet tenacity to dry tenacity to be at least about 0.1. High yield pulp fibers contain a high amount of lignin which facilitates the wet elasticity of the fibers. The resin bonds formed by the wet strength agent immobilize the wet elastic fibers in a sheetlike structure, which adapts to the structure of the belt on which through drying is effected. During the drying step, the bonds formed by the wet strength agent are cured so that wet-resistant bonds may form which, in turn, impart highly elastic properties to a corresponding web in a wet state. The web maintains this property because, in an UCTAD process, no creping step or other steps are performed which would destroy the bonds again. The UCTAD material is highly suitable to transfer and store liquids because the material is stabilized also in a wet state. Various advantages of the absorbent article of the invention shall now be explained in further detail.

The liquid-permeable top layer which is disposed toward the wearer's body may, for example, be made of a spun-bonded polypropylene. If suitable pigments, such as titanium oxide, are added to this liquid-permeable top cover layer, this layer prevents to a certain extent the liquid stored in the absorbent article from showing through. This bodyside top layer may also be a nonwoven or film material including a centrally disposed opening.

The next layer is the cover layer, which includes a central opening to facilitate penetration of discharged liquids into the layers further below. This opening may, for example, be punched out and exhibit an oval or dog-bone shape. The cover layer, too, may include pigments, which in turn prevents discharged and absorbed liquids from showing through on the surface of the absorbent article. The cover layer further serves to prevent liquid which has penetrated into the absorbent article from flowing back to the surface, so that no re-wetting occurs and the wearer's body is kept dry.

This is achieved with a cover layer which is constituted of a coform material. A suitable coform material is, for example, a polypropylene/pulp mixture with a polypropylene content of more than 50 wt. %. Polypropylene contents of 50 to 80 wt. %, in particular, 60 wt. %, were found to be particularly suitable. A coformr material is prepared using pulp that is defiberized and melt-blown polypropylene is prepared. The defiberized pulp and the polypropylene fibers are then mixed and laid on a moving belt, to obtain the desired polypropylene/pulp mixtures. Due to the structure of the coform material, i.e., due to its pulp content, this cover layer absorbs liquid discharged from above and transfers it downward. This is important, for example, when a sanitary napkin is improperly positioned and the liquid does not pass via the punched out opening directly through the foil into the sanitary napkin. The polypropylene, which accounts form more than 50% of the coform material, prevents liquid which has already penetrated into the sanitary napkin from being taken up by the cover layer from below. Accordingly, the coform material results in a considerable improvement of the rewetting properties of the absorbent article. If a corresponding pigmentation is added, absorbed liquid is prevented from showing through, and a so-called stain-hiding effect is achieved.

The rewetting properties of the absorbent article of the invention can further be improved if the cover layer is of a two-layered or three-layered construction. The upper bodyside layer may be the above-described coform material which is a mixture of polypropylene and pulp. This coform material is then preferably applied on a further layer of polymerized alkene, such as polypropylene. Three-layered structures having a coform layer sandwiched between two layers of polymerized alkene are also possible. The polypropylene may be prepared by means of spunbonding processes which result into a nonwoven-type structure. The hydrophobic properties of the polymer alkene effectively prevents liquid, once it has been absorbed in the absorbent body, from flowing back again to the surface of the absorbent article.

The compensation or surge layer is preferably made of a nonwoven material. The nonwoven can be made of polyethylene, polypropylene or other polymerized alkenes, and it can comprise bicomponent fibers. If the absorbent article is a diaper, this compensation layer both serves to store and to transfer the absorbed urine. However, if the absorbent article is a sanitary napkin, the compensation layer has no storage function. In sanitary napkins the compensation layer primarily serves again to keep absorbed liquid invisible.

Apart from nonwoven materials, carded webs can also be used for the compensation layer. Preferred compensation layers have been treated with a surface-active substance. Particularly suitable surface-active agents contain silicone. The surface active agents are applied on the underside of the compensation layer, i.e., on the side which rests on the absorbent body which provides secondary storage. The resulting capillary effects effectively prevent rewetting through the compensation layer.

The absorbent body has a particular function in the absorbent article. It serves to store and distribute liquid which has penetrated into the absorbent article. The liquid-distribution function of the absorbent body can be promoted by a special embossing, which locally increases the density of the absorbent body in longitudinal direction of the absorbent article. The densification can, for example, be effected by embossing lines or grooves. The embossing should at least be in that area which is positioned below the central opening of the cover layer. The embossing may, however, be further extended to the end portions of the absorbent body.

A preferred absorbent body comprises five densified portions extending in longitudinal direction. The embossings reduce the absorbent capacity of the absorbent body in the embossed portions. The penetrated liquid is distributed in the thus formed recesses and is transferred into the primary storage layer below. Moreover, due to the embossing, the thickness of the absorbent body is reduced in its central area, so that the thickness of the absorbent article is larger at the edges than in the central portion. This depression in the central portion increases the wear comport, for example, of a sanitary napkin. If liquid is then discharged on the absorbent body, due to the depression in the central portion, the sanitary napkin has less body contact with the wearer's skin which increases the feeling of dryness on the body surface. Pulp is a particularly suitable material for the absorbent body and the secondary storage, respectively.

The primary storage layer is positioned directly on the liquid-impermeable layer which serves as a garment-protecting foil. It is preferably made of an UCTAD material, tissue fluff or a melt-blown polypropylene. Apart from storing liquid, the primary storage layer serves to transfer penetrated liquid into the end portions of the absorbent body. The distribution into the end portions can even be promoted in that the primary layer is narrower in the central portion of the absorbent article than in the end portion. If the primary storage is made, for example, of tissue fluff, it is capable of absorbing up to about 2 ml of liquid. Tests have shown that no more than 2 ml of liquid are applied to more than half of all sanitary napkins before they are exchanged. This means that in the major part of used sanitary napkins the entire amount of absorbed liquid is taken up in the layer which is furthest remote from the wearer's body and contiguous to the garment-protecting foil. As a result, rewetting is optimally prevented and the absorbent liquid will not show through on the bodyside surface of the sanitary napkin. Should more than 2 ml be discharged, the primary storage layer releases any excess liquid upwardly into the secondary storage layer, resulting into the so-called "bottom-up-filling effect", but not until more than 2 ml of liquid have been discharged.

The primary storage layer may also be in the form of a corrugated or pleated web, the corrugation promoting the distributing function of the layer. The corrugations of the web are so arranged that the liquid is transferred in longitudinal direction to the ends of the article. The corrugations extend in cross-direction of the absorbent article such that they form transfer channels in longitudinal direction.

DETAILED DESCRIPTION OF THE PRESENTLY PREFERRED EMBODIMENTS

The present invention will now be explained with reference to the figures and preferred embodiments which are configured as sanitary napkins.

Figure 1:
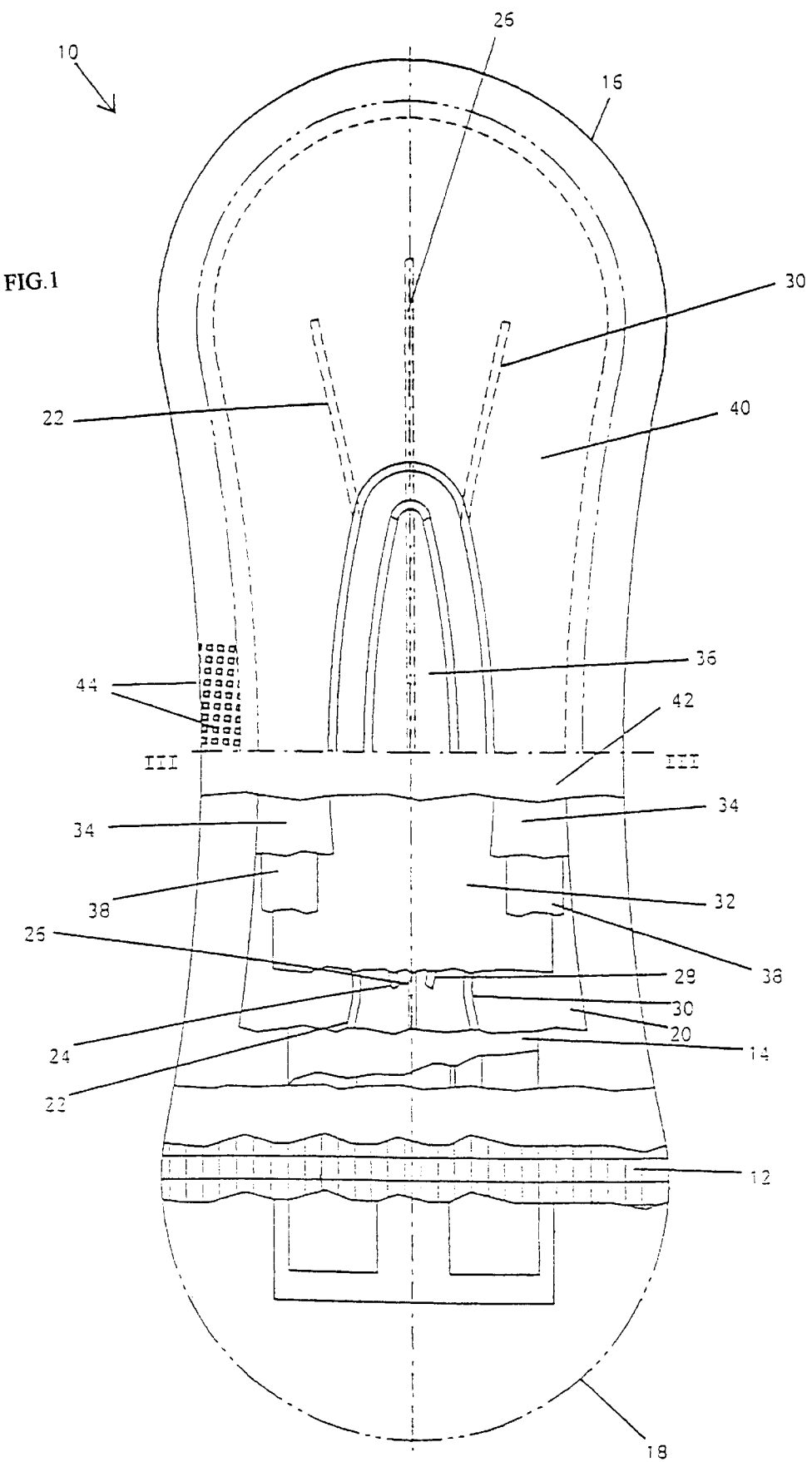
FIG. 1 is a top view of an absorbent article of the invention with oval-shaped central opening in the cover layer.

FIG. 1 is a top view of an absorbent article 10 of the invention. In the lower section of FIG. 1 sheets and layers, respectively, of the article 10 of the invention have in part been cut out to show the layers below. The lowermost layer of the article 10 is formed by a liquid-impermeable layer 12 which is shown in rectangular pattern. The liquid-impermeable layer 12 is made of a polypropylene foil. The liquid-impermeable layer 12 serves as so-called garment-protecting foil which prevents liquid which has penetrated into the absorbent article and which is retained therein from escaping downwards from the absorbent body. This prevents the wearer's undergarment from being stained.

The primary storage layer 14, which is made of a tissue fluff material, rests on the liquid-impermeable layer 12. The longitudinal edges of the webs forming the primary storage layer 14 are folded inwardly such that they overlap below the web, as shown in further detail in FIG. 3. The primary storage layer is capable of taking up and retaining about 2 ml of liquid. Furthermore, the primary storage layer 14 serves to distribute liquid which has penetrated into the central portion of the absorbent article 10 into the forward and rearward end portions 16 and 18 of the absorbent article.

The next layer is a secondary storage layer 20 made of a pulp sheet. Grooves 22, 24, 26, 28 and 30 are embossed into the pulp sheet. Liquid impinging on the secondary storage layer 20 is preferably further transported through the grooves 22, 24, 26, 28 and 30 to the forward and rearward portions of the absorbent article 10 and transferred downward into the primary storage layer 14. As a result of the embossed grooves 22, 24, 26, 28 and 30, the secondary storage layer 20 is locally densified. This locally reduces the absorbency of the secondary storage layer 20, which, in turn, facilitates the transfer of the penetrated liquid to the primary storage layer 14 below. This ensures that the primary storage layer 14 is allowed to be soaked with liquid before the secondary storage 20 is filled up with penetrated liquid. Only if the capacity limit of the primary storage layer 14 is exhausted, the latter releases liquid again to the secondary storage layer 20 above , which results into the so-called "bottom-up-filling effect".

On the secondary storage 20, a compensation layer 32 is situated. The compensation layer 32 consists of a nonwoven spunbonded polypropylene. It mainly serves to allow a rapid penetration of the liquid into the absorbent article and prevents the penetrated liquid from rewetting and showing through the surface of the absorbent article.

On the compensation layer 32, a cover layer 34 is situated. The cover layer 34 has an oval-shaped central opening 36.

The cover layer 34 is joined at the edges with the compensation layer 32 by means of a hot melt adhesive layer 38. This prevents said two layers from moving out of position relative to one another. The cover layer is made of a coform material of pulp and polypropylene, the amount of polypropylene of the mixture being 60 wt. %. Furthermore, a titanium oxide pigment is deposited in the oval-shaped opening. The central oval-shaped opening 36 is punched out during the manufacturing process of the cover layer.

The bodyside top sheet of the absorbent article of the invention according to FIG. 1 is formed by the liquid-permeable layer 40 made of spunbonded polypropylene nonwoven material, which includes titanium oxide for pigmentation. The liquid-permeable layer 40 is joined via a hot melt adhesive layer 42 with the cover layer 34, and in the area of the central opening 36 of the cover sheet 34 with the compensation layer 32, causing stabilization of the sheet structure of the absorbent article. A peripheral embossing 44 is provided at the outer periphery of the absorbent article 10.

Figure 2:
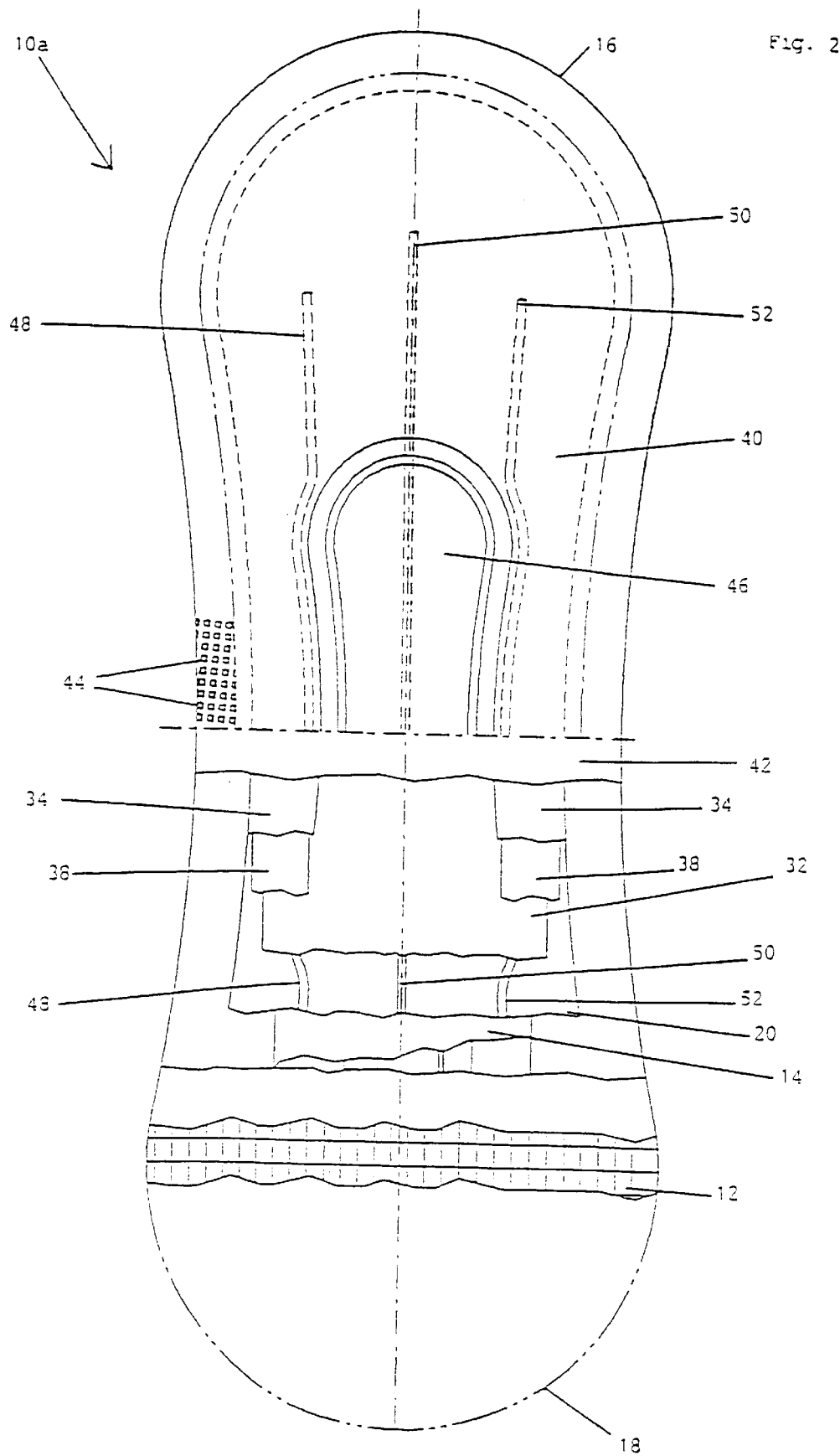
FIG. 2 is a top view of an absorbent article of the invention with a dogbone-shaped central opening in the cover layer.

FIG. 2 shows an absorbent article 10a, the basic structure of which corresponds to that described with reference to FIG. 1. The absorbent article 10a differs from the absorbent article 10 in the shape of the central opening of the cover sheet 34. The central opening 46 of the cover layer of the absorbent article 10a of the embodiment shown in FIG. 2 is of dogbone shape. Furthermore, the embossed grooves 48, 50, 52 are different from those of the absorbent article 10. Both configurations of the grooves ensure an effective distribution of penetrated liquid to the end portions (16, 18) of the absorbent article 10, 10a. The other elements of the absorbent articled 10a shown in FIG. 2 correspond to the elements of the absorbent article 10 shown in FIG. 1 and, accordingly, are designated by the same reference numbers.

Figure 3:
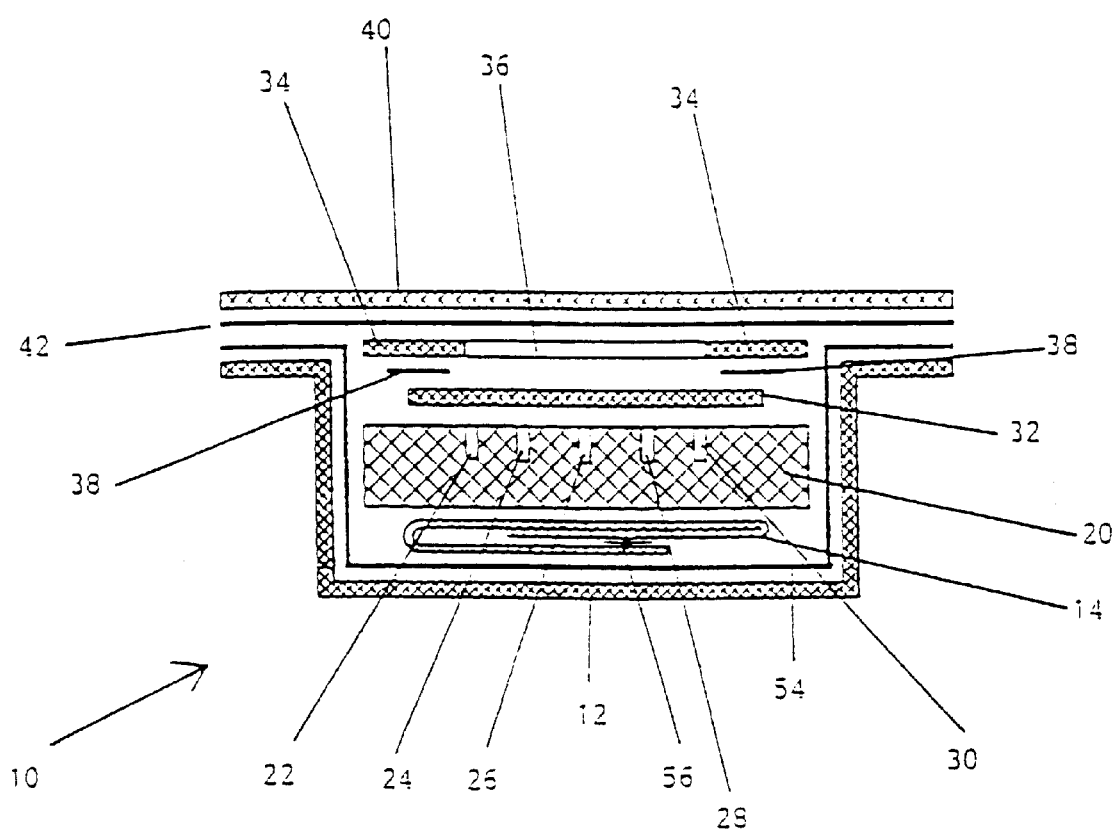
FIG. 3 is a cross-section through the absorbent article of the invention according to FIG. 1 along line III—III.

FIG. 3 shows a cross-section of the sanitary napkin shown in FIG. 1 along line III—III. Reference number 12 again designates the liquid-impermeable layer which serves as garment-protecting foil. The liquid-impermeable layer 12 is coated with a hot melt adhesive layer 54 which is not visible in FIG. 1. The primary storage layer 14 is applied on the hot melt adhesive layer 54. The primary storage layer 14 is folded inwardly at its edges, the inwardly folded ends thereof overlapping one another. The overlapping ends are bonded to one another by means of a hot melt adhesive line 56. The secondary storage layer 20 is provided on the primary storage layer 14. Grooves 22, 24, 26, 28 and 30 are embossed into the secondary storage layer 20. On the secondary storage layer 20 there is provided the compensation layer 32 which is joined to the cover layer 34 by means of the hot melt adhesive layer 38. The cover layer 34 includes the central oval-shaped opening 36. The top sheet of the absorbent article 10 of the present invention is formed by the liquid-permeable layer 40 which is joined to the layers beneath by mean s of the hot melt adhesive layer 42. When the absorbent article 10 of the invention is in use, the individual layers are pressed onto each other so that they are in direct contact with each other. For reasons of clarity, FIG. 3 shows the individual layers separated from one another.

Figure 4:
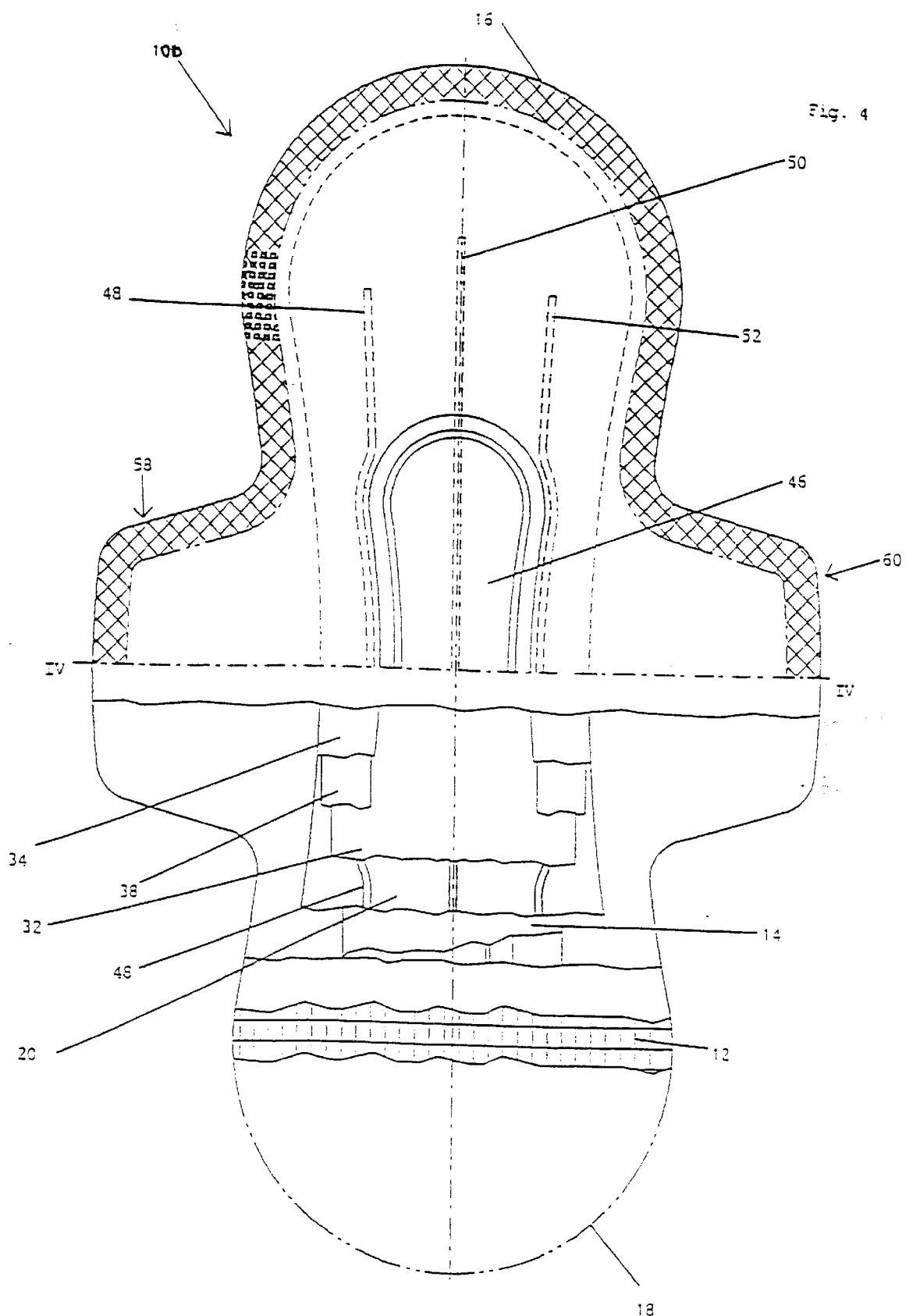
FIG. 4 is a top view of an absorbent article of the invention with flaps.

FIG. 4 shows a further embodiment of the absorbent article of the invention, the major structure of which corresponds to the absorbent article 10a shown in FIG. 2. In order for the absorbent article 10b to be better fastened to the wearer's garment, this absorbent article exhibits peripheral flap portions 58, 60. When the article 10b used, the flap portions are folded over downwardly and connected with one another at the outside of undergarment. Otherwise, the structure and the other reference numbers in FIG. 4 correspond to those in FIG. 2.

Figure 5:
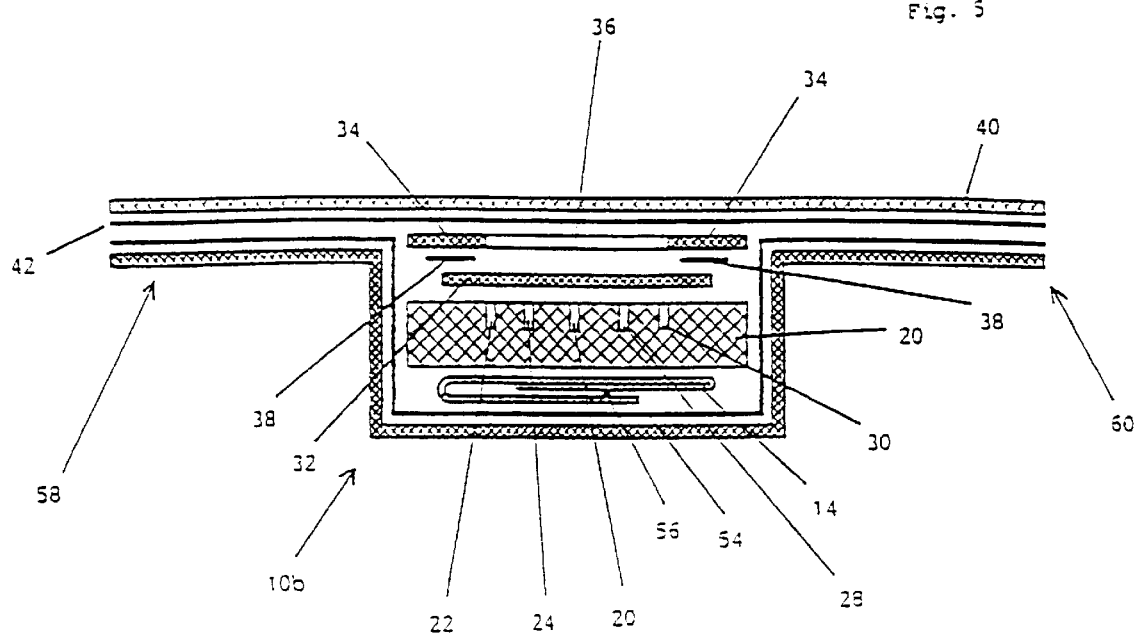
FIG. 5 is a cross-section through the absorbent article according to FIG. 4 along the line IV—IV.

FIG. 5 shows a cross section of the absorbent article 10b of FIG. 4 along the line IV—IV. The flap portions 58, 60 are also clearly visible in FIG. 5. Otherwise, the structure and the other reference numbers of FIG. 5 correspond to those of FIG. 3.

Figure 6:
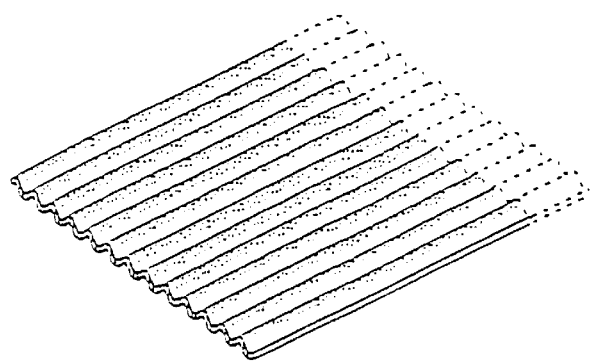
FIG. 6 is a perspective view of a primary storage layer in the form of a corrugated web.

Finally, FIG. 6 shows a corrugated web of an UCTAD material which can be used as primary storage layer 14 in the absorbent articles 10, 10a, 10b according to the invention. Due to the corrugation extending in cross-direction of the absorbent article, transfer channels are formed, which render the liquid distribution to the end portions 16, 18 of the absorbent article, on which liquid is discharged in the central portion, even more effective.

We claim:

1. An absorbent article, comprising
a liquid-impermeable bottom layer;
a primary storage layer above the liquid-impermeable layer;
a secondary storage layer above the primary storage layer;
a compensation layer above the secondary storage layer;
a cover layer above the compensation layer; and
a liquid-permeable top layer above the cover layer;
the cover layer having a central opening and including a mixture of pulp and at least 50% by weight polymerized alkene.

2. The absorbent article of claim 1, wherein the secondary storage layer comprises at least one densified section.

3. The absorbent article of claim 2, wherein the densified section extends in a longitudinal direction in the absorbent article.

4. The absorbent article of claim 2, wherein the densified section is below the central opening in the cover layer.

5. The absorbent article of claim 1, wherein the secondary storage layer comprises pulp.

6. The absorbent article of claim 1, wherein the cover layer comprises about 50–80% polymerized alkene.

7. The absorbent article of claim 1, wherein the polymerized alkene is selected from the group consisting of polyethylene, polypropylene, and combinations thereof.

8. The absorbent article of claim 1, wherein the cover layer further comprises a pigment.

9. The absorbent article of claim 8, wherein the pigment comprises titanium dioxide.

10. The absorbent article of claim 1, wherein the compensation layer comprises a nonwoven material.

11. The absorbent article of claim 8, wherein the nonwoven material comprises a polymerized alkene.

12. The absorbent article of claim 8, wherein the nonwoven material comprises bicomponent fibers.

13. The absorbent article of claim 1, wherein the primary storage layer comprises a material selected from UCTAD, tissue fluff, a polymerized alkene, and combinations thereof.

14. The absorbent article of claim 1, wherein the liquid-impermeable bottom layer comprises a film including a polymerized alkene.

15. The absorbent article of claim 1, wherein the liquid-permeable top layer comprises a nonwoven material including a polymerized alkene.

16. The absorbent article of claim 1, wherein the liquid-permeable layer has a central opening.

17. The absorbent article of claim 1, further comprising an adhesive on the liquid-impermeable layer.

18. The absorbent article of claim 1, further comprising lateral flaps.

19. An absorbent article, comprising:
a liquid-impermeable bottom layer;
a primary storage layer above the liquid-impermeable layer;
a secondary storage layer above the primary storage layer;
a compensation layer above the secondary storage layer;
a cover layer above the compensation layer; and
a liquid-permeable top layer above the cover layer;
the cover layer having a central opening and including a mixture of pulp and at least 50% by weight polymerized alkene, wherein the secondary storage layer comprises five densified sections.

20. The absorbent article of claim 19, wherein at least one of the densified sections extends in a longitudinal direction in the absorbent article.

21. The absorbent article of claim 19, wherein at least one of the densified sections is below the central opening in the cover layer.

22. An absorbent article, comprising:
a liquid-impermeable bottom layer;
a primary storage layer above the liquid-impermeable layer;
a secondary storage layer above the primary storage layer;
a compensation layer above the secondary storage layer;
a cover layer above the compensation layer; and
a liquid-permeable top layer above the cover layer;
the cover layer having a central opening and including a mixture of pulp and at least 50% by weight polymerized alkene, wherein the compensation layer comprises a surface coating including silicone.

23. An absorbent article, comprising:
a liquid-impermeable bottom layer;
a primary storage layer above the liquid-impermeable layer;
a secondary storage layer above the primary storage layer;
a compensation layer above the secondary storage layer;
a cover layer above the compensation layer; and
a liquid-permeable top layer above the cover layer;
the cover layer having a central opening and including a mixture of pulp and at least 50% by weight polymerized alkene, wherein the primary storage layer comprises a web having peripheral portions folded inward and overlapping each other.

24. An absorbent article, comprising:
a liquid-impermeable bottom layer;
a primary storage layer above the liquid-impermeable layer;
a secondary storage layer above the primary storage layer;
a compensation layer above the secondary storage layer;
a cover material above the compensation layer; and
a liquid-permeable top layer above the cover material;
the cover material having a central opening and comprising:
a first cover material layer including pulp and a polymerized alkene; and
a second cover material layer including a polymerized alkene.

25. The absorbent article of claim 24, wherein the first cover material layer faces the compensation layer.

26. The absorbent article of claim 24, wherein the second cover material layer faces the compensation layer.

27. An absorbent article, comprising:
a liquid-impermeable bottom layer;
a primary storage layer above the liquid-impermeable layer a secondary storage layer above the primary storage layer;

a compensation layer above the secondary storage layer;

a cover material above the compensation layer; and a liquid-permeable top layer above the cover material;

the cover material having a central opening and comprising:
- a first cover material layer including pulp and a polymerized alkene;
- a second cover material layer including a polymerized alkene; and
- a third cover material layer;
- the second and third cover material layers being positioned on both sides of the first cover material layer.

28. The absorbent article of claim 27, wherein the third cover material layer comprises a polymerized alkene.

29. The absorbent article of claim 24, wherein at least one of the cover material layers comprises a pigment.

30. The absorbent article of claim 29, wherein the pigment comprises titanium dioxide.

31. A sanitary napkin, comprising:

a liquid-impermeable bottom layer;

a primary storage layer above the liquid-impermeable layer;

a secondary storage layer above the primary storage layer;

a compensation layer above the secondary storage layer;

a cover layer above the compensation layer; and a liquid-permeable top layer above the cover layer;

the cover layer having a central opening and including a mixture of pulp and at least 50% by weight polymerized alkene.

32. A feminine care liner, comprising:

a liquid-impermeable bottom layer;

a primary storage layer above the liquid-impermeable layer;

a secondary storage layer above the primary storage layer;

a compensation layer above the secondary storage layer;

a cover layer above the compensation layer; and a liquid-permeable top layer above the cover layer;

the cover layer having a central opening and including a mixture of pulp and at least 50% by weight polymerized alkene.

* * * * *

UNITED STATES PATENT AND TRADEMARK OFFICE
CERTIFICATE OF CORRECTION

PATENT NO. : 6,573,424 B1
DATED : June 3, 2003
INVENTOR(S) : Raidel et al.

It is certified that error appears in the above-identified patent and that said Letters Patent is hereby corrected as shown below:

Column 7,
Line 46, should read -- The absorbent article of claim 10, wherein the non- --
Line 48, should read -- The absorbent article of claim 10, wherein the non- --

Signed and Sealed this

Seventh Day of October, 2003

JAMES E. ROGAN
*Director of the United States Patent and Trademark Office*